United States Patent [19]

Wolters et al.

[11] Patent Number: 5,700,934
[45] Date of Patent: Dec. 23, 1997

US005700934A

[54] PROCESS FOR THE PREPARATION OF EPSILON-CAPROLACTAM AND EPSILON-CAPROLACTAM PRECURSORS

[75] Inventors: Henricus F. W. Wolters, Echt, Netherlands; Samuel L. Lane, Beaumont, Tex.; Wim Buijs, Schinnen; Nicolaas F. Haasen, Sittard, both of Netherlands; Frank E. Herkes, Wilmington, Del.

[73] Assignees: DSM N.V., Heerlen, Netherlands; E. I. DuPont de Nemours & Company, Wilmington, Del.

[21] Appl. No.: 616,742

[22] Filed: Mar. 15, 1996

Related U.S. Application Data

[63] Continuation-in-part of Ser. No. 396,240, Mar. 1, 1995, abandoned, and Ser. No. 565,594, Nov. 30, 1995, abandoned.

[51] Int. Cl.$^6$ ................................................ C07D 201/08
[52] U.S. Cl. .................. 540/538; 564/197; 564/198; 560/196; 562/553
[58] Field of Search ...................... 540/538; 564/197, 564/198; 560/196; 562/553

[56] References Cited

U.S. PATENT DOCUMENTS

| | | | |
|---|---|---|---|
| 3,485,821 | 12/1969 | Sheehan | 260/239.3 |
| 4,730,040 | 3/1988 | Vagt | 540/538 |
| 4,730,041 | 3/1988 | Hutmacher | 540/538 |
| 4,731,445 | 3/1988 | Hutmacher | 540/538 |
| 4,766,237 | 8/1988 | Hutmacher | 560/155 |
| 4,950,429 | 8/1990 | Vagt | 562/553 |
| 4,963,672 | 10/1990 | Merger | 540/538 |
| 5,055,618 | 10/1991 | Kampmann | 564/473 |
| 5,068,398 | 11/1991 | Merger | 560/156 |
| 5,475,141 | 12/1995 | Kos | 564/473 |

FOREIGN PATENT DOCUMENTS

| | | |
|---|---|---|
| 0 628 535 | 12/1994 | European Pat. Off. |
| 47-10715 | 5/1972 | Japan |
| 4-329148 | 11/1992 | Japan |

*Primary Examiner*—Robert T. Bond
*Attorney, Agent, or Firm*—Cushman Darby & Cushman IP Group of Pillsbury Madison & Sutro, LLP

[57] ABSTRACT

A process for the preparation of ε-caprolactam and ε-caprolactam precursors, starting from the corresponding 5-formylvalerate ester, ammonia and hydrogen in the presence of a hydrogenation catalyst is disclosed, wherein in a step (a) 5-formylvalerate ester is reacted with ammonia under non-hydrogenating conditions, and in a step (b) the reaction product obtained in step (a) is converted to ε-caprolactam and the ε-caprolactam precursor(s) under hydrogenating conditions, in the presence of ammonia.

14 Claims, No Drawings

PROCESS FOR THE PREPARATION OF EPSILON-CAPROLACTAM AND EPSILON-CAPROLACTAM PRECURSORS

RELATED APPLICATIONS

This application is a continuation-in-part of application 08/396,240 filed Mar. 1, 1995, abandoned and of its continuation application 08/565,594 filed Nov. 30, 1995, abandoned, the complete disclosures of which are incorporated herein by reference.

FIELD OF THE INVENTION

The invention relates to a process for the preparation of ε-caprolactam and ε-caprolactam precursors, starting from 5-formylvalerate ester, ammonia and hydrogen in the presence of a hydrogenation catalyst. ε-Caprolactam precursors are here defined as 6-aminocaproate ester, 6-aminocaproic acid and 6-aminocaproamide.

BACKGROUND OF THE INVENTION

According to U.S. Pat. No. 4,730,040, a mixture of ε-caprolactam and 6-aminocaproate esters is prepared by contacting 5-formylvalerate esters with ammonia, hydrogen a hydrogenation catalyst and methanol as solvent.

This known process suffers from undesirable drawbacks. In particular, relatively large quantities of by-products are formed which decreases the yield of 6-aminocaproate ester and ε-caprolactam. These by-products include 6-hydroxycaproate esters, secondary amines, tertiary amines and Schiff bases. Indeed, within only several hours of continuous operation, the yields obtained from this known process decrease significantly.

Thus, there is a need for a process for making ε-caprolactam and ε-caprolactam precursors which does not produce large quantities of undesirable by-products. Furthermore, there is a need for a continuous process for making ε-caprolactam and ε-caprolactam in which significant yields can be maintained.

SUMMARY AND OBJECTS OF THE PRESENT INVENTION

An object of the present invention is to provide a process which avoids the problems caused by large quantities of by-products. Another object of the invention is to provide a continuous process which maintains a significant yield of ε-caprolactam and ε-caprolactam precursors.

These and other objects are achieved by the present invention. The present invention provides a process in which in (a) 5-formylvalerate ester is reacted with ammonia under non-hydrogenating conditions and (b) the reaction product obtained in the step (a) is converted to ε-caprolactam and ε-caprolactam precursors under hydrogenating conditions in the presence of ammonia.

It has been found that, surprisingly, if the process is performed according to the invention, significantly less by-products are formed, especially 6-hydroxycaproate esters and secondary amines. An additional advantage is that the yield remains constant over a long period of time when the process is carried out continuously. This is in contrast to the significant decreases in yield encountered when the process of U.S. Pat. No. 4,730,040 is performed continuously over a long period of time.

DETAILED DESCRIPTION OF THE INVENTION

5-Formylvalerate ester can be represented by the following general formula:

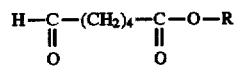

where R represents an organic group having 1 to about 20 carbon atoms. Suitable examples of R include a (cyclo)alkyl, an aryl or an aralkyl group, such as, methyl, ethyl, propyl, isopropyl, n-butyl, tert-butyl, isobutyl, cyclohexyl, benzyl and phenyl. Preferably, methyl or ethyl are used.

The step (a) is carried out under non-hydrogenating conditions. Preferably, the non-hydrogenating conditions means that the reaction conditions are such that substantially no hydrogen is present. The non-hydrogenating conditions also includes the presence of hydrogen under conditions such that the 5-formylvalerate esters or reaction products thereof are not significantly reduced by the hydrogen. In general, the presence of non-hydrogenating conditions can be achieved by carrying out the first step in the absence of a hydrogenation catalyst.

The hydrogen can be present in step (a) if no hydrogenation catalyst is present. If a hydrogenation catalyst is present in step (a), a situation of non-hydrogenating conditions can also be realized by not adding hydrogen to the reaction mixture until after completing step (a).

It has been found that the best results with regard to yield to 6-aminocaproate ester are achieved when the conversion of 5-formylvalerate ester in step (a) is more than about 90%, preferably more than about 99%. Too low of a conversion can result in an increase of, for example, the 6-hydroxycaproate ester and/or formation of secondary amines. In general, too low of a conversion is less than about 90%. It has further been found that this yield can be negatively influenced when the residence or contact time in step (a) is greater than the residence time or contact time needed for a virtually complete conversion of the 5-formylvalerate ester. An excessively long residence or contact time can cause increased formation of by-products other than 6-hydroxycaproate ester. Accordingly, it is preferred to avoid "overreacting" step (a).

The temperature in the step (a) may be up to about 120° C. and is preferably between about 0° C. to about 100° C. The temperature is not very critical within this range. In a large scale operation the temperature will preferably be above about 10° C. and more preferably above about 20° C., because excessive cooling will most likely not be required. When step (a) is performed in a continuously operated tube reactor the feed temperature can be for example, above about 10° C. Because heat is produced by the exothermic reaction, the temperature of the reaction mixture may rise so that at the end of the reactor a higher outlet temperature is achieved.

As explained above a low contact or residence time and a high contact or residence time in step (a) may result in undesirable by-product formation. A residence or contact time during which the conversion of 5-formylvalerate ester is virtually completed will depend on the reaction conditions, for example temperature, concentration of reactants and method of mixing. The residence time or contact time required to obtain virtually complete conversion can be easily determined by a person skilled in the art based on the disclosure provided herein. Based on the temperature and concentration ranges described herein, a suitable residence or contact time has been found to be between about several seconds to about 2 minutes. Preferably the contact or residence time is higher than about 5 seconds.

The step (a) is carried out in the presence of ammonia. Preferably, a molar excess of ammonia is selected so that the molar ratio ammonia and 5-formylvalerate esters is between about 500:1 and about 1:1 calculated from the starting amount of 5-formylvalerate ester.

The pressure in step (a) is not critical. If step (a) is carried out in the absence of hydrogen, the pressure is, in general, between atmospheric pressure and about 12 MPa, depending on the temperature and the composition of the reaction mixture that have been selected. In a continuous process the pressure in steps (a) and (b) can be about the same.

The step (a) can be carried in the presence of a catalyst, for example an acid ion exchanger or an acidic metal oxide catalyst, for example alumina or $TiO_2$. The conversion of 5-formylvalerate ester in the step (a) also proceeds favorably in the absence of a catalyst. Because the overall yield to 6-aminocaproate ester may not be greatly influenced by the presence of a catalyst in step (a), such a catalyst is generally not used.

The reaction product obtained in step (a) is converted in step (b), completely or partly to ε-caprolactam and ε-caprolactam precursors, under hydrogenating conditions in the presence of ammonia. Preferably, step (b) is carried out in the presence of an excess of ammonia such that the molar ratio ammonia and 5-formylvalerate ester is between about 500:1 and about 1:1 calculated from the starting amount of 5-formylvalerate ester (used in step (a)).

The term 'hydrogenating conditions' means that the reaction conditions are such that the reaction product(s) obtained in step (a) can be reduced by hydrogen. In general hydrogenation conditions are achieved when hydrogen and a hydrogenation catalyst are present.

The molar quantity of hydrogen needed for step (b) is generally at least equal to the molar quantity of the 5-formylvalerate ester which was started from in the first step. Preferably, about a 1.01 to about a hundred fold molar excess of hydrogen is used in step (b).

The total pressure used in step (b) is preferably between about 0.5 and about 20 MPa. It has been found that an efficacious pressure in step (b) will also depend on the optional solvent used. However, a person skilled in the art can readily ascertain efficacious reaction conditions with a limited set of experiments based on the disclosure provided herein.

In the process according to the invention, at least one of steps (a) and (b), if desired, can be carried out in the presence of an additional solvent. Ammonia may also serve as the solvent of the process. If an additional solvent is used, preferably the second step is performed in the presence of the additional solvent. More preferably, both steps are performed in the presence of an additional solvent. Suitable solvents include water, tertiary amines, alcohols having 1–6 carbon atoms, ethers having 2 to 10 carbon atoms, for example methyl-tertiary butyl ether and tertiary amylmethyl ether or high boiling organic solvents, for example a high boiling paraffin solvent. The additional solvent(s) is preferably an alcohol, an ether or water. When an alcohol solvent is used, the one corresponding to the R-group (formula (1)) of the 5-formylvalerate ester is preferred. Water and the corresponding alcohol are preferred solvents because these compounds are also formed as a reaction product in the process according to the invention. Examples of these include methanol, ethanol, propyl alcohol, isopropyl alcohol, n-butyl alcohol, tert-butyl alcohol, isobutyl alcohol, cyclohexyl alcohol, benzyl alcohol and phenol or mixtures thereof, of which methanol and ethanol are most preferred. Mixtures of additional solvents may also be used in the process according to the invention. Examples of such mixtures are water-methanol, water-ethanol or methyl-ethanol.

Most preferably water or water-corresponding alcohol mixtures are used as solvent in both steps. These mixtures of water and corresponding alcohol are advantageous because the 5-formylvalerate ester has increased solubility in these mixtures compared to pure water. Water is advantageous because it can also be used as solvent in a cyclization step following the process according to the invention. In such a cyclization step the ε-caprolactam precursors are converted to ε-caprolactam at elevated temperature such as, for example, described in U.S. Pat. No. 3,485,821, the complete disclosure of which is incorporated herein by reference. When using water as solvent in the process according to the invention the reaction mixture obtained can be directly used in such a cyclization.

Step (b) can be carried out at a temperature, for example, between about 40° and about 200° C., more preferably between about 70° and about 180° C. and most preferably between about 80° and about 160° C.

The residence or contact time in the step (b) is preferably high enough to reduce virtually all the intermediate products formed in the first step. Generally, more ε-caprolactam is formed at a longer residence time or a longer contact time. The residence or contact time is preferably between about a half minute to a couple of hours, such as, for instance 2 hours. When the process is carried out batch wise or in a continuously operated slurry reactor, the contact or residence time respectively will generally be higher than the residence time than when a continuously operated tube reactor is used.

The hydrogenation catalyst, for example, comprises at least one metal selected from among the metals of Groups 8–10 of the Periodic System of the Elements (Handbook of Chemistry and Physics, 70th edition, CRC Press, 1989–1990). Preferably, the hydrogenation catalyst is a Ru-, Ni- or Co-containing catalyst. In addition to Ru, Co and/or Ni the catalysts can also contain other metals such as for example Cu, Fe and/or Cr. The catalytically active metals may, if desired, be applied onto a carrier. Suitable carriers include, among others, aluminum oxide, silica, titanium oxide, magnesium oxide, zirconium oxide and carbon. Non-carried metals can be used for example in the form of a finely dispersed suspension, such as, for example, finely dispersed ruthenium. Preferred Ni- and Co-containing catalysts are Raney nickel and Raney cobalt optionally in combination with small amounts of another metal, for example Cu, Fe and/or Cr.

It has been discovered that the yield of ε-caprolactam and ε-caprolactam precursors can be maximized by adjusting the reaction conditions of the second step. These reaction conditions are for example temperature, pressure, ammonia/5-formylvalerate ratio and the presence or absence of an additional solvent. The conditions to obtain a yield for given operations can be easily ascertained by a person skilled in the art based on the disclosure provided herein.

The two step process according to the invention can be performed batch wise or continuous. A large scale commercial process will preferably be performed continuously. For step (a), it is important that the reactants are sufficiently contacted at the desired temperature during the desired period of time as described above. Any manner of contacting will usually suffice. For example a tube reactor with or without, for example, internal baffling or packing or a static mixer is a possible contacting unit for the first step. To control the temperature in step (a) it may be advantageous to use cooling devices, for example cooled walls or a cooling spiral placed in the contacting unit.

Step (b) may be performed in a fixed bed reactor in which for example the heterogeneous hydrogenation catalyst is present. An advantage of this reactor is that the reactants are easily separated from the hydrogenation catalyst. Another manner of operating the step (b) is by way of one or more continuously well mixed contactors in series in which the hydrogenation catalyst is present as a slurry (slurry reactor). This manner of operation has the advantage that the heat of reaction can be easily controlled such as by a cooled feed or by way of internally placed cooling devices. An example of a specific and suitable slurry reactor is a one or multiple staged bubble column or a gas lift-loop reactor.

The concentration of 5-formylvalerate ester and the products of the process (ε-caprolactam and ε-caprolactam precursors) in the reaction mixture in both steps is preferably between about 1 and about 50 wt. % and more preferably is between about 10 and about 35 wt. %.

The invention will be further elucidated by means of the following non-limiting examples.

The yields in the Examples I–V were calculated as mol product relative to mol starting 5-formylvalerate. Surprisingly, a practically 100% conversion of 5-formylvalerate was achieved in all Examples.

EXAMPLE I

Preparation of methyl 6-aminocaproate and ε-caprolactam from methyl 5-formylvalerate (M5FV) without using an additional solvent.

Two tubular reactors were arranged in series. The first reactor consisted of a 150 mm long tube with a diameter of 3.2 mm. Ammonia and M5FV were fed at room temperature. The ammonia/M5FV molar ratio was 28:1. M5FV was supplied at a rate of 40 l/h (ammonia: 132 g/h). The residence time in this reactor was 17 seconds (sec.). The feed streams of the first reactor have a temperature of 20° C. No measures were taken to control the temperature in the first reactor. The outlet temperature was 77° C.

The second reactor consisted of a 430 mm long vertical tube with a diameter of 8 mm. The reactants were pumped upward through the reactor. This reactor was heated over its full length. The second reactor was filled with 10 g of an activated catalyst comprising 1 wt. % Ru on aluminum oxide. The empty volume above the catalyst bed was filled with glass beads. The total pressure was 9.6 MPa. The hydrogen flux was 35 normal l/h. The inlet temperature of the second reactor was 77° C. and the outlet temperature in the second reactor was 127° C. The liquid residence time was 3 minutes. The experiment was run for 2 hours in which the yields remained constant during this period. The molar yields determined by means of Gas Chromatography-mass Spectrometry (GC-MS), were 85% of methyl 6-aminocaproate and 4% of ε-caprolactam.

EXAMPLE II

Example I was repeated except that a stream of M5FV solution (20% by weight M5FV in methanol) was pumped at a rate of 210 ml/h and 96 grams/h ammonia together with a stream of hydrogen at a rate of 20 standard l/h through the two reactors. The total pressure was 9.2 MPa.

The first reactor was kept at 20° C. by using a cooling coil. The temperature in the second reactor was maintained at 129° C.

The residence time in the first reactor was 12 seconds and in the second reactor 130 seconds.

The molar yields based on M5FV turned out to be 96.5% by weight methyl 6-aminocaproate and 3.4% by weight ε-caprolactam. The experiment was run for 4 hours in which the above results remained constant during this period.

EXAMPLE III

Example II was repeated except that 18% by weight solution of M5FV in methanol was used.

The solution of M5FV in methanol was fed at a rate of 210 ml/h into the first one of the two reactors together with ammonia at a rate of 65 grams/h. Both liquids were fed at room temperature. The yield based on M5FV turned out to be 97.5% methyl 6-aminocaproate and 2.5% ε-caprolactam.

COMPARATIVE EXPERIMENT A

Preparation of methyl 6-aminocaproate from M5FV without the first reactor, and using methanol as solvent.

Ammonia, a 16.8 wt. % mixture of M5FV in methanol and hydrogen were directly fed to the bottom of the second reactor filled with 1% Ru on aluminum oxide (Johnson Matthey). The ammonia/M5FV molar ratio was 13.5:1. Hydrogen was pumped through the reactor at a rate of 20 l/hr. The total pressure was 10 MPa. The temperature was set at 129° C.

The yields, based on the converted M5FV turned out to be 83% methyl-6-aminocaproate, 2% 6-aminocaproic amide and 2% ε-caprolactam. The total conversion after 1 hour was 92%. The conversion after 2 hours was 70% and after 3 hours only 48%. The selectivity, the total amount of 6-aminocaproic amide, ε-caprolactam and methyl 6-aminocaproate with respect to the total amount of converted M5FV went down from 87% after 1 hour to 35% after 3 hours.

EXAMPLE IV

A vertically placed fixed-bed reactor (diameter=8 mm, total length=43 cm and fill height=30 cm) with electrical heating was filled with 10.3 g of an activated catalyst consisting of ruthenium on an alumina carrier (3 wt. % ruthenium; diameter of catalyst particles was 1 mm). An hourly supply of 20 Nl hydrogen (0.8 mol), 140 ml of a 9 wt. % solution of methyl 5-formylvalerate in methyl tert-butyl ether and 116 ml (4 mol) of liquid ammonia was fed to this reactor. Prior to feeding the reactants to the fixed bed reactor the reactants were continuously mixed in a first step at 20° C. and 9.6 MPa in a volume of approximately 7 ml (residence time of approximately 100 seconds). The resulting mixture was passed over the catalyst from bottom to top at a temperature of 130° C. and a pressure of 9.6 MPa (residence time approximately 1.5 minutes). The reaction mixture was discharged from the top of the fixed-bed reactor and after cooling the over-pressure was let off. From quantitative High Pressure Liquid Chromatography (HPLC) analysis it appeared that all the methyl 5-formylvalerate had been converted and that the molar yield of methyl 6-aminocaproate was 88%, while the yield of ε-caprolactam was 10%, relative to the quantity of starting methyl 5-formylvalerate. The combined yield of methyl 6-aminocaproate and ε-caprolactam together was 98%.

EXAMPLE V

Example IV was repeated in which the same volume of liquid ammonia was used instead of methyl tert-butyl ether. The yield of methyl 6-aminocaproate and ε-caprolactam was 94%. All of the methyl 5-formylvalerate had been converted.

EXAMPLE VI

At a pressure of 5.0 MPa, 45 g/hr of methyl-5-formylvalerate, 495 g/hr of water and 360 g/hr of ammonia was pumped through a tube which was cooled by a water bath so that a constant temperature of 35° C. was maintained in the tube. Almost no back mixing occurred and the (liquid) residence time was 15 seconds. The resulting mixture leaving the tube (first step) was fed to a continuously stirred tank reactor (CSTR), a Hastelloy C autoclave of 1 liter liquid volume. The reactor was stirred at 1250 rpm. The residence time was 60 minutes and the temperature was kept at 100° C. To the reactor, 10 g/hr of hydrogen was fed. The reactor was filled with 50 g of an unpromoted Raney Nickel catalyst (93 wt. % nickel and 7 wt. % aluminum, average particle size: 30 μm from Activated Metals Company (A5000)).

The effluent was analyzed by HPLC after 3 and 6 hours of operation. The results are summarized in Table 1. The yields after 3 and 6 hours of operation were comparable and within their respective error range. The conversion of methyl 5-formylvalerate was 100%.

TABLE 1

|  | 3 hours | 6 hours |
|---|---|---|
| 6-aminocaproamide | 58.7(1) | 59.8 |
| 6-aminocaproic acid | 23.9 | 25.3 |
| methyl-6-aminocaproate | 0.4 | 0.0 |
| ε-caprolactam | 17.0 | 14.9 |

(1)Results in weight percentage.

As is clear from Table 1 high yields of ε-caprolactam and ε-caprolactam precursors, up to a total of 100%, were obtained.

EXAMPLE VII

Example VI was repeated for 50 hours at a pressure of 3 MPa, in which 81.7 g/hr of methyl-5-formylvalerate (M5FV), 203 g/hr ammonia and 526 g/hr water was pumped through the tube at a temperature of 35° C. Almost no back-mixing occurred in the tube and the liquid residence time in the tube was 15 seconds. The reaction mixture leaving the tube contained no M5FV.

The mixture leaving the tube was fed to the continuously stirred tank reactor (CSTR) in which a liquid hold-up of 1 liter of liquid was maintained. The catalyst in the CSTR was a 5 wt % ruthenium on $Al_2O_3$ catalyst (Engelhard: ESCAT 44) and the catalyst concentration was maintained at 103 g/l. The CSTR was stirred at 1260 rpm. The pressure in the CSTR was kept constant at 3 MPa and the temperature at 120° C. The residence time was 60 minutes. To the reactor a net amount of 5.0 g/hr of hydrogen was fed.

The effluent of the CSTR was analyzed by High Pressure Liquid Chromatography (HPLC) every 4 hours. The composition of the effluent did not vary significantly during the 50 hours of operation. The average composition of the effluent in the last 28 hours was 28 mol % 6-aminocaproic acid (6ACA), 47.2 mol % 6-aminocaproic acid amide (6ACAM), 24.2 mol % ε-caprolactam (CAP), 0.6 mol % methyl 6-aminocaproate (M6AC). Thus a 100 mol % yield to ε-caprolactam and δ-caprolactam precursors was obtained.

EXAMPLE VIII

Example VII was repeated for 22 hours, except that the water feed was replaced by a mixture of water and methanol (15 wt % methanol). The feed rate of this mixture was 511 g/hr. Almost no back-mixing occurred in the tube and the liquid residence time in the tube was 15 seconds. The reaction mixture leaving the tube contained practically no methyl-5-formylvalerate.

The catalyst concentration in the CSTR was 96.0 g/l.

The composition of the effluent did not vary significantly during the 22 hours of operation. The average composition of all the products formed in the last 12 hours was 22.5 mol % 6ACA, 48.0 mol % 6ACAM, 27.4 mol % ε-caprolactam, 2.1 mol % methyl 6-aminocaproate. Thus a 100 mol % yield to ε-caprolactam and ε-caprolactam precursors is obtained.

What is claimed is:

1. A process for the preparation of ε-caprolactam and ε-caprolactam precursor, starting from the corresponding 5-formylvalerate ester, ammonia and hydrogen in the presence of a hydrogenation catalyst, comprising the combination of steps of:

(a) reacting said 5-formylvalerate ester with ammonia under non-hydrogenating conditions to obtain a reaction product; and (b) converting the reaction product obtained in step (a) to ε-caprolactam and the ε-caprolactam precursor(s) under hydrogenating conditions in the presence of ammonia.

2. A process according to claim 1, wherein said 5-formylvalerate ester is represented by the following general formula

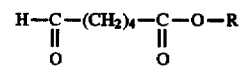

wherein R has 1 to 20 carbon atoms and is a $C_1$–$C_{20}$ a (cyclo)alkyl, an aryl or an aralkyl group.

3. A process according to claim 1 or 2, wherein the process is carried out in the presence of an ether having 2 to 10 carbon atoms.

4. A process according to claim 1 or 2, wherein the process is carried out in the presence of methyl-tertiary butyl ether.

5. A process according to claim 2, wherein R is methyl or ethyl.

6. A process according to claim 2 or 5, wherein steps (a) and (b) are performed in the presence of an additional solvent, wherein the solvent is a mixture of water and an alcohol represented by ROH.

7. A process according to claim 1, 2 or 5, wherein in step (a) is carried out in the absence of a hydrogenation catalyst.

8. A process according to claim 1, wherein more than 90% of the 5-formylvalerate ester is converted in step (a).

9. A process according to claim 1, wherein the temperature in the step (a) is between about 0° to about 100° C.

10. A process according to claim 1, wherein a molar excess of ammonia is present in step (a) and step (b).

11. A process according to claim 1, wherein step (b) is carried out at a temperature between about 70° and about 180° C.

12. A process according to claim 1, wherein step (b) is carried out in the presence of a hydrogenation catalyst comprising at least one metal selected from Groups 8–10 of the Periodic System of the Elements.

13. A process according to claim 12, wherein the catalyst contains at least one of the metals Ni, Co or Ru.

14. A process according to claim 1, wherein step (a) and step (b) are performed continuously.

* * * * *